(12) United States Patent
Tsuji et al.

(10) Patent No.: US 9,161,695 B2
(45) Date of Patent: Oct. 20, 2015

(54) APPARATUS FOR EVALUATING VASCULAR ENDOTHELIAL FUNCTION

(75) Inventors: Toshio Tsuji, Hiroshima (JP); Masao Yoshizumi, Hiroshima (JP); Yukihito Higashi, Hiroshima (JP); Masashi Kawamoto, Hiroshima (JP); Hideo Ozawa, Tokyo (JP); Teiji Ukawa, Tokyo (JP); Tsuneo Takayanagi, Tokyo (JP)

(73) Assignees: NIHON KOHDEN CORPORATION, Tokyo (JP); HIROSHIMA UNIVERSITY, Hiroshima (JP)

( * ) Notice: Subject to any disclaimer, the term of this patent is extended or adjusted under 35 U.S.C. 154(b) by 690 days.

(21) Appl. No.: 12/878,374

(22) Filed: Sep. 9, 2010

(65) Prior Publication Data
US 2011/0066048 A1    Mar. 17, 2011

(30) Foreign Application Priority Data
Sep. 14, 2009  (JP) .................................. 2009-212533

(51) Int. Cl.
    A61B 5/02    (2006.01)
(52) U.S. Cl.
    CPC .............. *A61B 5/02* (2013.01); *A61B 5/02007* (2013.01)
(58) Field of Classification Search
    USPC .................................................. 600/485–515
    See application file for complete search history.

(56) References Cited

U.S. PATENT DOCUMENTS

| | | | | |
|---|---|---|---|---|
| 2002/0002339 | A1* | 1/2002 | Sugo et al. | 600/485 |
| 2002/0133082 | A1 | 9/2002 | Ogura | |
| 2003/0216652 | A1 | 11/2003 | Narimatsu et al. | |
| 2004/0092832 | A1 | 5/2004 | Schnall et al. | |
| 2005/0070805 | A1* | 3/2005 | Dafni | 600/492 |
| 2005/0159663 | A1 | 7/2005 | Smith et al. | |
| 2005/0228303 | A1 | 10/2005 | Hayano et al. | |
| 2006/0178585 | A1 | 8/2006 | Sharrock | |
| 2009/0259131 | A1* | 10/2009 | Tsuji et al. | 600/493 |
| 2010/0292592 | A1* | 11/2010 | Parfenov et al. | 600/507 |
| 2010/0298717 | A1* | 11/2010 | Parfyonov et al. | 600/481 |

FOREIGN PATENT DOCUMENTS

| | | |
|---|---|---|
| EP | 1992282 A1 | 11/2008 |
| JP | 08-332173 A | 12/1996 |
| JP | 2002-272688 A | 9/2002 |
| JP | 3632014 A | 3/2005 |
| JP | 2006181261 A | 7/2006 |
| JP | 2007-044364 A | 2/2007 |
| JP | 2007209492 A | 8/2007 |
| JP | 4049671 B2 | 2/2008 |
| JP | 2012-526613 A | 11/2012 |

OTHER PUBLICATIONS

Extended European Search Report issued on Feb. 1, 2011 in the corresponding European Patent Application No. 10176310.0.

(Continued)

*Primary Examiner* — Michael Kahelin
*Assistant Examiner* — Mitchell E Alter
(74) *Attorney, Agent, or Firm* — Sughrue Mion, PLLC

(57) ABSTRACT

An apparatus for evaluating a vascular endothelial function using a first cuff that occludes an artery of a patient, measuring pulse waves from pressure of a second cuff at a different position than the first cuff, and evaluating the vascular endothelial function using the pulse waves.

8 Claims, 17 Drawing Sheets

(56) References Cited

OTHER PUBLICATIONS

Office Action dated Mar. 19, 2013, issued by the Japanese Patent Office in corresponding Japanese Patent Application No. 2009-212533.
Teiji Ozawa, "Evaluation of vascular endothelial function by the changes in volume pulse wave, pulse wave velocity and acceleration pulse wave in reactive hyperemia", Japanese Society of Clinical Physiology magazine, vol. 31, No. 4, 2001, 13 pgs. total.
Office Action, dated Sep. 5, 2013, issued by the Japanese Patent Office in counterpart Japanese Patent Application No. 2009-212533.
Communication from the European Patent Office issued Jun. 10, 2015 in a counterpart European Application No. 10176310.0.

* cited by examiner

FIG. 10

| MAXIMAL BLOOD PRESSURE | 165mmHg |
|---|---|
| MINIMAL BLOOD PRESSURE | 95mmHg |
| MEAN BLOOD PRESSURE | 110mmHg |
| RATIO OF PULSE WAVE AMPLITUDES | 1.1 |

FIG. 13

| | FIRST WEEK | SECOND WEEK | THIRD WEEK | FOURTH WEEK | FIFTH WEEK |
|---|---|---|---|---|---|
| MAXIMAL BLOOD PRESSURE | 165mmHg | 170mmHg | 130mmHg | 128mmHg | 125mmHg |
| MINIMAL BLOOD PRESSURE | 95mmHg | 98mmHg | 88mmHg | 78mmHg | 76mmHg |
| MEAN BLOOD PRESSURE | 110mmHg | 115mmHg | 98mmHg | 95mmHg | 93mmHg |
| RATIO OF PULSE WAVE AMPLITUDES | 1.05 | 1.06 | 1.11 | 1.38 | 1.45 |

APPARATUS FOR EVALUATING VASCULAR ENDOTHELIAL FUNCTION

BACKGROUND OF THE INVENTION

The present invention relates to an apparatus for evaluating a vascular endothelial function in which the evaluation similar to that obtained in a measurement using an ultrasonic echo system is enabled without using an ultrasonic echo system or the like.

Recently, researches that atherosclerosis develops while showing deterioration of the vascular endothelial function as the initial phase have been conducted. In order to prevent atherosclerosis, techniques and apparatuses for evaluating the vascular endothelial function have been developed.

As a reliable technique for evaluating the vascular endothelial function, there is an apparatus called an FMD (Flow-Mediated Dilation) measurement system. In the apparatus, measurement is performed in the following manner. A cuff which is similar to that for measuring the blood pressure is attached to the arm of the subject. After occlusion of the artery is performed for a constant time of about five minutes at a pressure which is higher than the maximal blood pressure of the subject, the occlusion of the artery is released. At about three minutes after the release of the occlusion of the artery, the vessel diameter at the upstream or downstream of the cuff is measured by an ultrasonic echo system. Based on the time-dependent change rate of the vessel diameter, the vascular endothelial function is evaluated.

In the case of a normal vessel, the production of nitric monoxide (NO) which is a vasodepressor material from vascular endothelial cells is promoted by shear stress of the inner wall of the vessel due to a blood flow immediately after the occlusion of the artery. As a result, the vessel diameter is expanded. By contrast, in the case where a disorder exists in the vascular endothelial function, the degree of the expansion of the vessel diameter is decreased. When the change in vessel diameter before and after the occlusion of the artery is measured, therefore, it is possible to evaluate the vascular endothelial function.

The evaluation technique by the FMD measurement system requires skills in measurement of the vessel diameter by an ultrasonic echo system, and is difficult to handle. Furthermore, there is a problem in that the technique requires a large-scale apparatus and lacks in simplicity.

By contrast, as a technique using a simple configuration, there is a technique using a cuff pressure. In the technique, the cuff pressure is maintained at a predetermined pressure (first pressure) which is higher than the maximal blood pressure, thereafter rapidly lowered, maintained at another predetermined pressure (second pressure) which is higher than the minimal blood pressure and lower than the mean blood pressure, and, during when the cuff pressure is maintained at the other predetermined pressure (second pressure), a ratio of a cuff pressure peak value of a first pulse wave which initially appears to the maximal cuff pressure peak value which thereafter appears is calculated, thereby enabling the vascular endothelial function to be evaluated (see Patent Reference 1).

As a technique in which an index of the vascular endothelial function can be accurately measured by a simple method, there is a technique in which pressure and volume pulse waves of a vessel to be measured are measured, a ratio of variations of the pulse waves per unit time is obtained, and, with respect to the third root of the maximum value of the ratio of variations of one heartbeat cycle at rest, a ratio to a value after release of occlusion of the artery is calculated as the degree of vasodilation (Patent Reference 2).

There is another technique in which, based on the time-dependent change of posterior pulse wave information indicating a feature of the posterior half portion which is after the peak of a pulse wave reflecting variations of the vessel diameter, it is determined whether the function of vascular endothelial cells is normal or not (Patent Reference 3).

There is a further technique in which a digit probe for measuring a change of the peripheral arterial pulsatile flow is attached to a finger tip, occlusion of the artery is performed for a constant time period while attaching a cuff to the same finger tip, and a change of the peripheral arterial tone before and after the occlusion of the artery is monitored (Patent Reference 4).

In the technique disclosed in Patent Reference 1, the pressurizing periods for the pressure stimulation and the pulse wave measurement are continuous to each other. Although the pressurization for the pulse wave measurement is lower than the artery mean blood pressure, the vein blood flow is blocked, and hence the burden on the subject is large.

In the technique disclosed in Patent Reference 2, in addition to the cuff for the pressure stimulation, a sensor for measuring the volume and pressure pulse waves must be disposed. Therefore, the operation is complicated.

In the technique disclosed in Patent Reference 3, a reflected wave component which is contained in the pressure pulse wave, and which is originated from peripheral vessels is measured. Measurement of the reflected wave component and calculation of an amplitude augmentation factor AI necessitate complicated waveform recognizing and calculating processes, and an analyzing unit must have a high processing capacity.

The vascular compliance is changed by the blood pressure. When the blood pressure is high, the vessel wall is in a state where the wall is extended in the circumferential direction and hardened, and the compliance is low. Conversely, when the blood pressure is low, a force acting on the vessel wall is small. Therefore, the vessel wall is extended in a smaller degree in the circumferential direction, and the compliance is high. All of the techniques disclosed in Patent References 1, 2, and 3 have a problem in that the measured vessel information is inevitably affected by the intravascular pressure, i.e., the blood pressure.

In the technique of Patent Reference 4, a change of the peripheral arterial tone is monitored by the digit probe. In the case where amplitudes of pulse waves are compared to each other, however, the possibility that unwanted influences are included is high. Particularly, the peripheral arterial tone is caused also by the sympathetic control. Consequently, there is a problem in that the technique cannot always correctly detect the vascular endothelial function.

In view of the above-discussed circumstances, the inventors have proposed a related-art apparatus in which a cuff is wound around a part of the body, occlusion of the artery is performed for a predetermined time period by using the cuff, the pulse wave is detected by using the cuff at the same position before and after the occlusion of the artery or the like, and the detected pulse wave is analyzed to evaluate the vascular endothelial function (JP-A-2009-273870).

It has been proved that, according to the related-art apparatus, the vascular endothelial function can be adequately evaluated by using one cuff. In the related-art apparatus, the pulse wave is detected at the position where the vessel is blocked due to occlusion of the artery, ischemia due to vascular blockage therefore exerts an influence in a portion where the pulse wave is measured, and hence it is seemed that the accuracy is slightly inferior to that of a measurement using an ultrasonic echo system.

[Patent Reference 1] JP-A-2007-209492
[Patent Reference 2] JP-A-2006-181261
[Patent Reference 3] Japanese Patent No. 3,632,014
[Patent Reference 4] Japanese Patent No. 4,049,671

SUMMARY

It is therefore an object of the invention to provide an apparatus for evaluating a vascular endothelial function in which the vascular endothelial function can be evaluated highly accurately without using an ultrasonic echo system and in a similar manner as a measurement using an ultrasonic echo system.

In order to achieve the object, according to the invention, there is provided an apparatus for evaluating a vascular endothelial function, the apparatus comprising: a first cuff, to be wound around a first body part of a subject; a second cuff, to be wound around a second body part of the subject; a cuff pressure controller, configured to control a cuff pressure of each of the first and second cuffs, and configured to perform continuous pressure stimulation on the first body part of the subject for a time period by using the first cuff; a cuff pressure detector, configured to detect the cuff pressure of the second cuff from an output of a pressure sensor connected to the second cuff; a pulse wave detector, configured to detect, from the output of the pressure sensor, pulse waves before and after the continuous pressure stimulation is performed; and an analyzer, configured to evaluate the vascular endothelial function by comparing the pulse waves detected before and after the continuous pressure stimulation is performed.

The analyzer may obtain an amplitude ratio of the pulse waves detected before and after the continuous pressure stimulation is performed.

The continuous pressure stimulation performed by the cuff pressure controller may be a constant pressure.

The cuff pressure controller may perform, at least one time, processing that includes a first process and a second process subsequent to the first process, at least one of before and after performing the continuous pressure stimulation, the first process in which the cuff pressure of the second cuff is raised from an atmosphere pressure to a pressure that is equal to or higher than a mean blood pressure of the subject, the second process in which the cuff pressure of the second cuff is lowered to a pressure that is equal to or lower than a minimal blood pressure. The analyzer may apply statistical processing on change of the pulse waves while the cuff pressure controller performs the processing.

The statistical processing may be processing in which a maximum value in amplitudes of the pulse waves detected in the first process or the second process is obtained.

The cuff pressure controller may perform processing in which the cuff pressure of the second cuff is a constant pressure, at least one of before and after performing the continuous pressure stimulation. The analyzer may apply statistical processing in which a maximum value in amplitudes of the pulse waves while the cuff pressure controller performs the processing is obtained.

The statistical processing may be processing in which an average value of a neighborhood of a maximum value in amplitudes of the pulse waves while the cuff pressure controller performs the processing is obtained.

The cuff pressure controller may perform processing in which the cuff pressure of the second cuff is a constant pressure, at least one of before and after performing the continuous pressure stimulation. The analyzer may apply statistical processing in which an average value of a neighborhood of a maximum value in amplitudes of the pulse waves while the cuff pressure controller performs the processing is obtained.

The analyzer may perform processing in which an amplitude of each of the pulse waves is divided by a difference between a maximal blood pressure of the subject and a minimal blood pressure of the subject, to obtain vascular compliance.

The apparatus may further include a display. The analyzer may calculate a blood pressure value from each of the pulse waves, and the display may display the blood pressure value together with a comparison result of the pulse waves.

The first body part around which the first cuff is wound and the second body part around which the second cuff is wound may be parts of one of four limbs of a body of the subject.

The first body part around which the first cuff is wound may be placed on a peripheral side of a body of the subject with respect to the second body part around which the second cuff is wound.

According to the invention, there is also provided an apparatus for evaluating a vascular endothelial function, the apparatus comprising: a cuff, to be wound around a body part of a subject; a cuff pressure controller, configured to control a cuff pressure of the cuff, and configured to perform continuous pressure stimulation on the body part of the subject for a time period by using the cuff; a cuff pressure detector, configured to detect the cuff pressure of the cuff from an output of a pressure sensor connected to the cuff; a pulse wave detector, configured to detect, from the output of the pressure sensor, pulse waves before and after the continuous pressure stimulation is performed; and an analyzer, configured to evaluate the vascular endothelial function by comparing the pulse waves detected before and after the continuous pressure stimulation is performed, wherein the cuff pressure controller performs, at least one time, processing that includes a first process and a second process subsequent to the first process, at least one of before and after performing the continuous pressure stimulation, the first process in which the cuff pressure of the cuff is raised from an atmosphere pressure to a pressure that is equal to or higher than a mean blood pressure of the subject, the second process in which the cuff pressure of the second cuff is lowered to a pressure that is equal to or lower than a minimal blood pressure, and the analyzer applies statistical processing on change of the pulse waves while the cuff pressure controller performs the processing.

According to the invention, there is also provided an apparatus for evaluating a vascular endothelial function, the apparatus comprising: a cuff, to be wound around a body part of a subject; a cuff pressure controller, configured to control a cuff pressure of the cuff, and configured to perform continuous pressure stimulation on the body part of the subject for a time period by using the cuff; a cuff pressure detector, configured to detect the cuff pressure of the cuff from an output of a pressure sensor connected to the cuff; a pulse wave detector, configured to detect, from the output of the pressure sensor, pulse waves before and after the continuous pressure stimulation is performed; and an analyzer, configured to evaluate the vascular endothelial function by comparing the pulse waves detected before and after the continuous pressure stimulation is performed, wherein the cuff pressure controller performs processing in which the cuff pressure of the cuff is a constant pressure, at least one of before and after performing the continuous pressure stimulation, and the analyzer applies statistical processing on change of the pulse waves while the cuff pressure controller performs the processing.

The statistical processing may be processing in which a maximum value in amplitudes of the pulse waves while the cuff pressure controller performs the processing is obtained.

The statistical processing may be processing in which an average value of a neighborhood of a maximum value in amplitudes of the pulse waves while the cuff pressure controller performs the processing is obtained.

BRIEF DESCRIPTION OF THE DRAWINGS

FIG. 10 is a view showing an example of information displayed by the embodiment of the apparatus according to the invention.

FIG. 13 is a view showing an example of information displayed by the embodiment of the apparatus according to the invention.

DETAILED DESCRIPTION OF EMBODIMENTS

Figure 1:
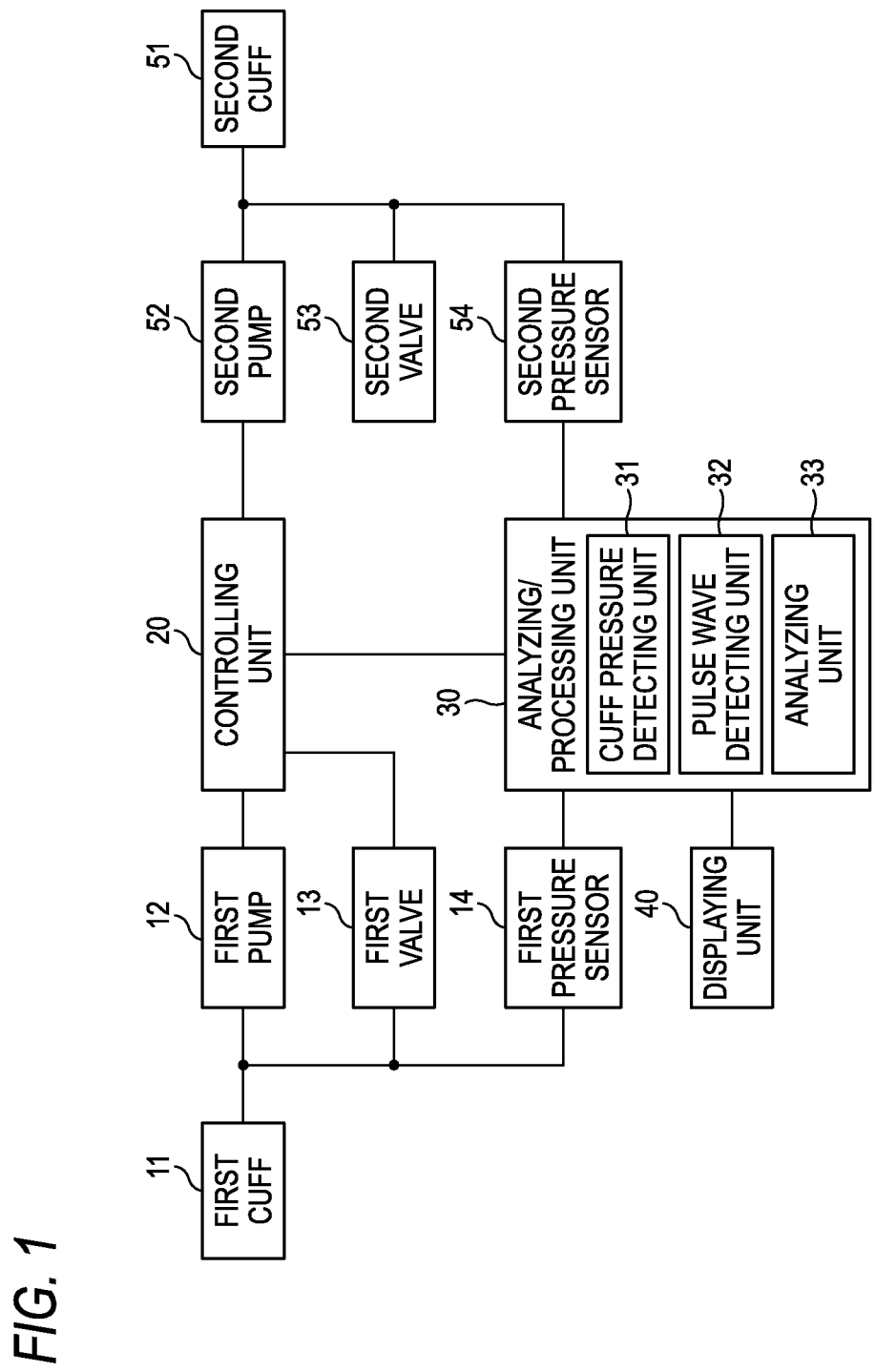
FIG. 1 is a diagram showing the configuration of an embodiment of the apparatus for evaluating a vascular endothelial function according to the invention.
Figure 2:
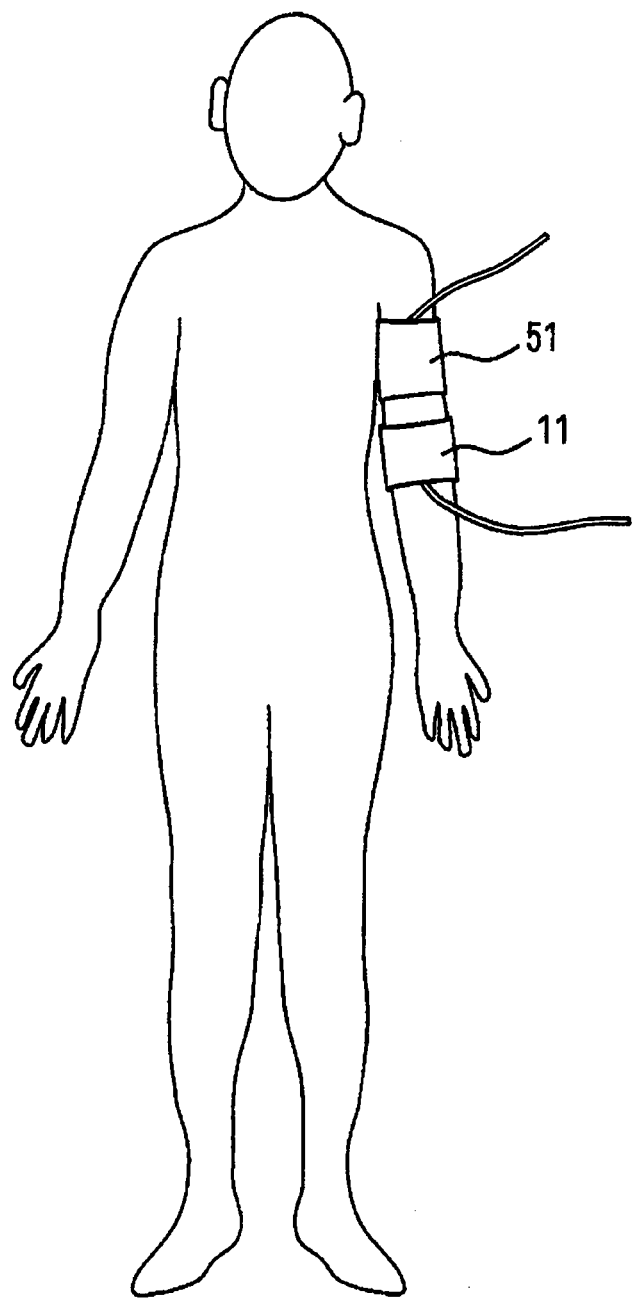
FIG. 2 is a view illustrating a state where cuffs of the embodiment of the apparatus according to the invention are attached to the body.

FIG. 1 is a diagram showing the configuration of an apparatus for evaluating a vascular endothelial function according to an embodiment of the invention. The apparatus includes a first cuff 11, a first pump 12, a first valve 13, a first pressure sensor 14, a controlling unit 20, an analyzing/processing unit 30, and a displaying unit 40. A second pump 52 and a second valve 53 are connected to the controlling unit 20. A second pressure sensor 54 is connected to the analyzing/processing unit 30. Furthermore, a second cuff 51 is connected to the second pump 52, the second valve 53, and the second pressure sensor 54. The first cuff 11 is to be wound around a first body part such as an arm or leg of the subject, and used for applying a pressure for occlusion of the artery on the portion around which the cuff is wound. The second cuff 51 is to be wound around a second body part such as an arm or leg of the subject, and used for applying a pressure for pulse wave detection on the portion around which the cuff is wound. In a measurement, preferably, for example, the first cuff 11 is wound around an arm portion of the arm, and the second cuff 51 is wound around a portion which is on the upstream side (the side which is closer to the heart) of the first cuff 11 as shown in FIG. 2.

The first pump 12 feeds the air into the first cuff 11 under the control of the controlling unit 20. The first valve 13 switches non-discharging/discharging of the air in the first cuff 11 under the control of the controlling unit 20. The second pump 52 feeds the air into the second cuff 51 under the control of the controlling unit 20. The second valve 53 switches non-discharging/discharging of the air in the second cuff 51 under the control of the controlling unit 20. The controlling unit 20 controls pressurization and depressurization of the first cuff 11 and the second cuff 51.

The first pressure sensor 14 is connected to the first cuff 11, and outputs a signal corresponding to the pressure in the first cuff 11, and the second pressure sensor 54 is connected to the second cuff 51, and outputs a signal corresponding to the pressure in the second cuff 51. The analyzing/processing unit 30 is configured by, for example, a computer, controls the whole apparatus, and includes a cuff pressure detecting unit 31, a pulse wave detecting unit 32, and an analyzing unit 33. In the embodiment, for the sake of convenience, the controlling unit 20 which controls the first cuff 11 and the second cuff 51, and the analyzing/processing unit 30 which performs analysis and processing are commonly used. Alternatively, they are disposed for each of the cuffs.

The cuff pressure detecting unit 31 detects the cuff pressures of the first and second cuffs 11, 51 from outputs of the first and second pressure sensors 14, 54. The pulse wave detecting unit 32 detects a pulse wave from the output of the second pressure sensor 54. The analyzing unit 33 analyzes the detected pulse wave.

Figure 3A:
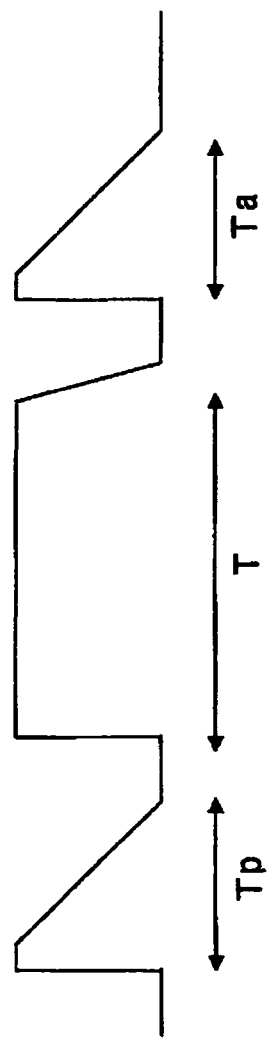
FIGS. 3A and 3B are views showing first examples of a pulse wave measurement which is performed by the embodiment of the apparatus according to the invention, and a period of occlusion of the artery.

The controlling unit 20 performs continuous pressure stimulation for a predetermined time period, on a part of the body of the subject, and changes the cuff pressure as shown in, for example, FIG. 3A. Namely, vascular endothelial stimulation is executed during a pressurization period (a period of occlusion of the artery) T by using the first cuff 11, and the pulse wave amplitude is measured before and after the pressurization period T, i.e., during measurement periods Tp and Ta by using the second cuff 51. For example, the pressurization period T may be set to about five minutes, and the pressurization periods Tp and Ta may be set to a time which is required for usual blood pressure measurement. During the pressurization period T, the output of the first pressure sensor 14 is monitored, and occlusion of the artery is performed at a pressure which is a sum of the maximal blood pressure and a predetermined pressure (for example, 50 mmHg).

Figure 4:
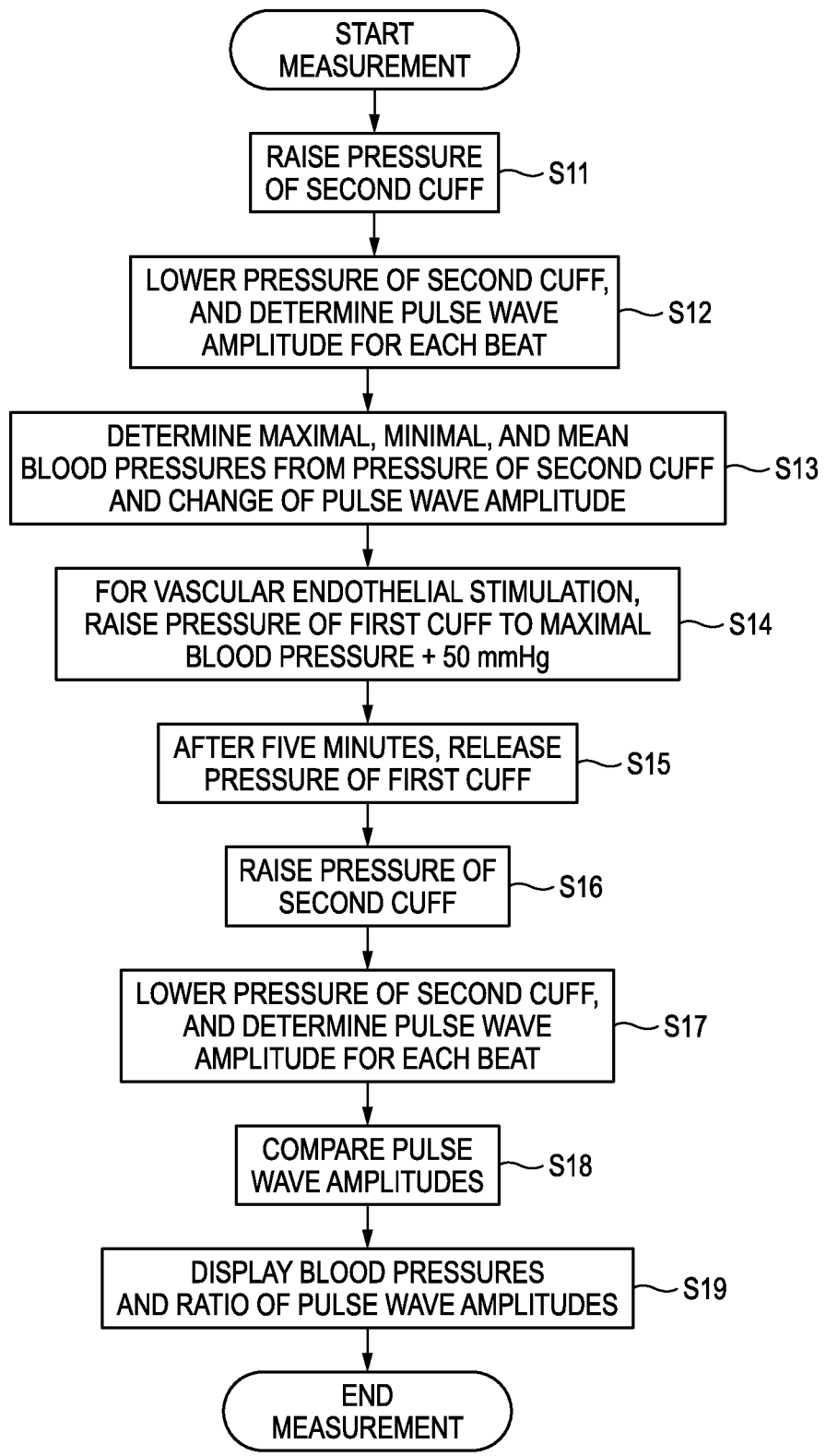
FIG. 4 is a flowchart illustrating a pulse wave measuring operation which is performed in a process of depressurizing a cuff pressure by the embodiment of the apparatus according to the invention.

The apparatus for evaluating a vascular endothelial function performs processing shown in the flowchart of FIG. 4. As described above, the first cuff 11 is wound around an arm portion which is a part of the body of the subject as shown in, for example, FIG. 2, the second cuff 51 is wound around an arm portion which is a part of the body of the subject, and which is on the upstream side of the first cuff 11, and then the measurement is started. Under the control of the controlling unit 20, in a state where the second valve 53 is closed, the air is sent from the second pump 52 to the second cuff 51 to raise the cuff pressure (S11).

When the cuff pressure reaches a predetermined pressure, the air supply from the second pump 52 is stopped, and the second valve 53 is opened. Therefore, the cuff pressure is lowered, and the pulse wave detecting unit 32 detects the pulse wave amplitude for each beat (S12).

Figure 3B:

Furthermore, the cuff pressure detecting unit 31 detects the cuff pressure from the output of the second pressure sensor 54, and, on the basis of the cuff pressure and the pulse wave amplitude, the analyzing unit 33 determines the maximal, minimal, and mean blood pressures, and obtains a representative pulse wave amplitude (S13). The representative pulse wave amplitude is obtained by statistically processing the pulse wave amplitude which is obtained in the pressurization period Tp. The pulse wave amplitude in the pressurization period Tp is obtained as shown in FIG. 3B, and hence the maximum pulse wave amplitude A is obtained. In the pressurization period Tp, when the cuff pressure is equal to the mean blood pressure, the pulse wave amplitude is maximum, and the amplitude is set as the maximum pulse wave amplitude A. In the case where the mean blood pressure is previously known, therefore, pressurization to a pressure which is equal to or higher than the mean blood pressure is not necessary in order to obtain the maximum pulse wave, and the burden on the subject is reduced.

Next, the pressurization period T when, in a state where the first valve 13 is closed under the control of the controlling unit 20, air is sent from the first pump 12 to the first cuff 11, and, for vascular endothelial stimulation, occlusion of the artery is performed at a pressure which is a sum of the maximal blood pressure and the predetermined pressure (for example, 50 mmHg) is realized (S14). After five minutes, the first valve 13 is opened to release the cuff pressure, whereby the cuff pressure is lowered to a pressure which is equal to or lower than the minimal blood pressure (S15). Thereafter, the second valve 53 is closed, and air is sent from the second pump 52 to raise the cuff pressure (S16). Furthermore, the cuff pressure of the second cuff 51 is lowered in a similar manner as described above, and the pulse wave detecting unit 32 detects the pulse wave amplitude for each beat (S17).

In a similar manner as step S13, on the basis of the cuff pressure and the pulse wave amplitude, the analyzing unit 33 determines the maximal, minimal, and mean blood pressures, and obtains a representative pulse wave amplitude B (S17). The representative pulse wave amplitude A and the representative pulse wave amplitude B are compared with each other to evaluate the vascular endothelial function (S18). The comparison is performed by obtaining a result of a division in which the representative pulse wave amplitude B is divided by the representative pulse wave amplitude A.

In the measurement of the pulse wave amplitude for each beat, the cuff pressure of the second cuff 51 may be raised from an atmosphere pressure to a pressure that is equal to or higher than the mean blood pressure, and then the cuff pressure may be lowered to a pressure that is equal to or lower than the minimal blood pressure.

Figure 5:
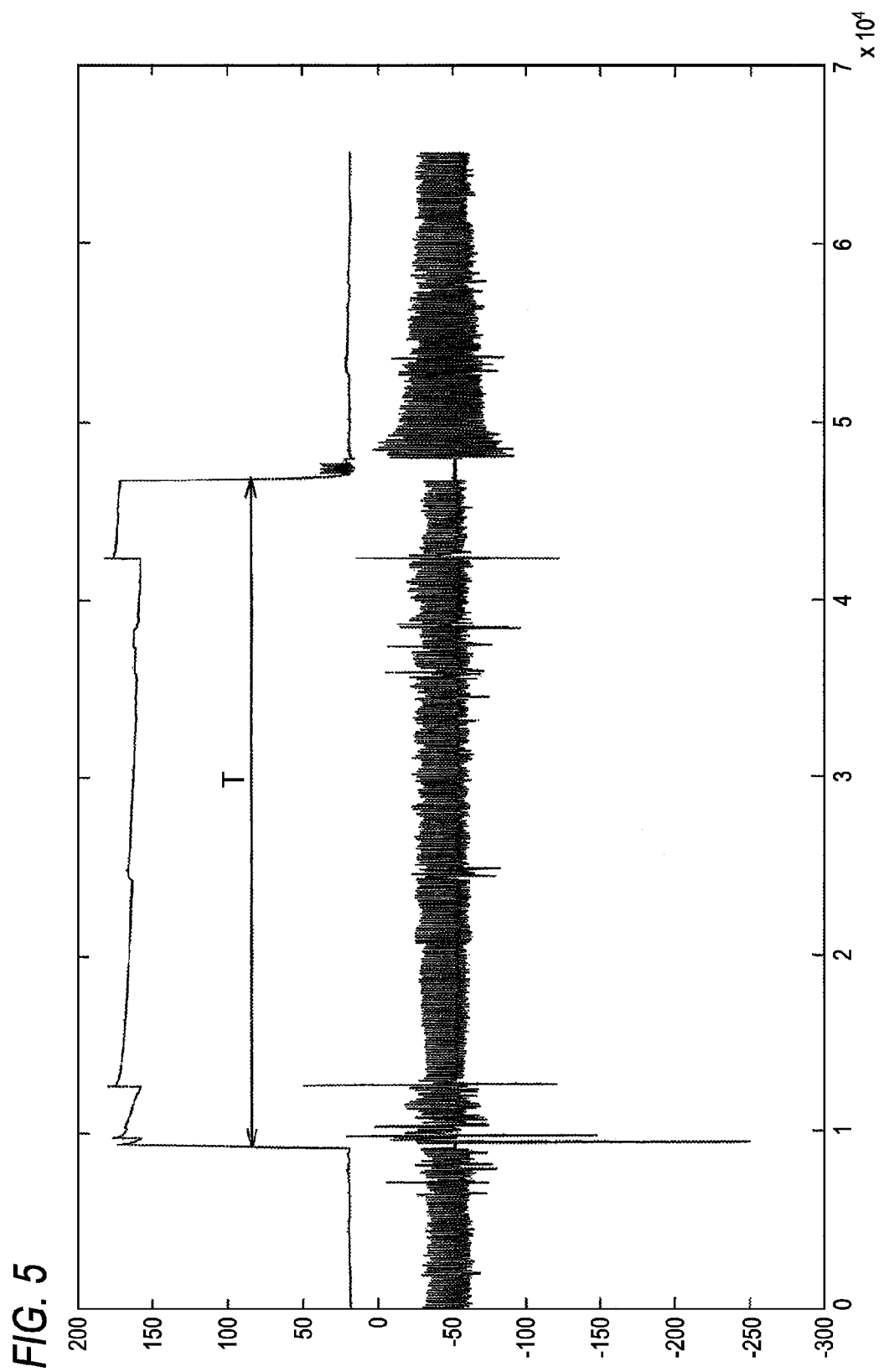
FIG. 5 is a view showing a change of a pulse wave amplitude in the case where the pulse wave measurement is performed after the period of the occlusion of the artery by the related-art apparatus for evaluating a vascular endothelial function in which the occlusion of the artery and the pulse wave measurement are performed in the same portion.
Figure 6:
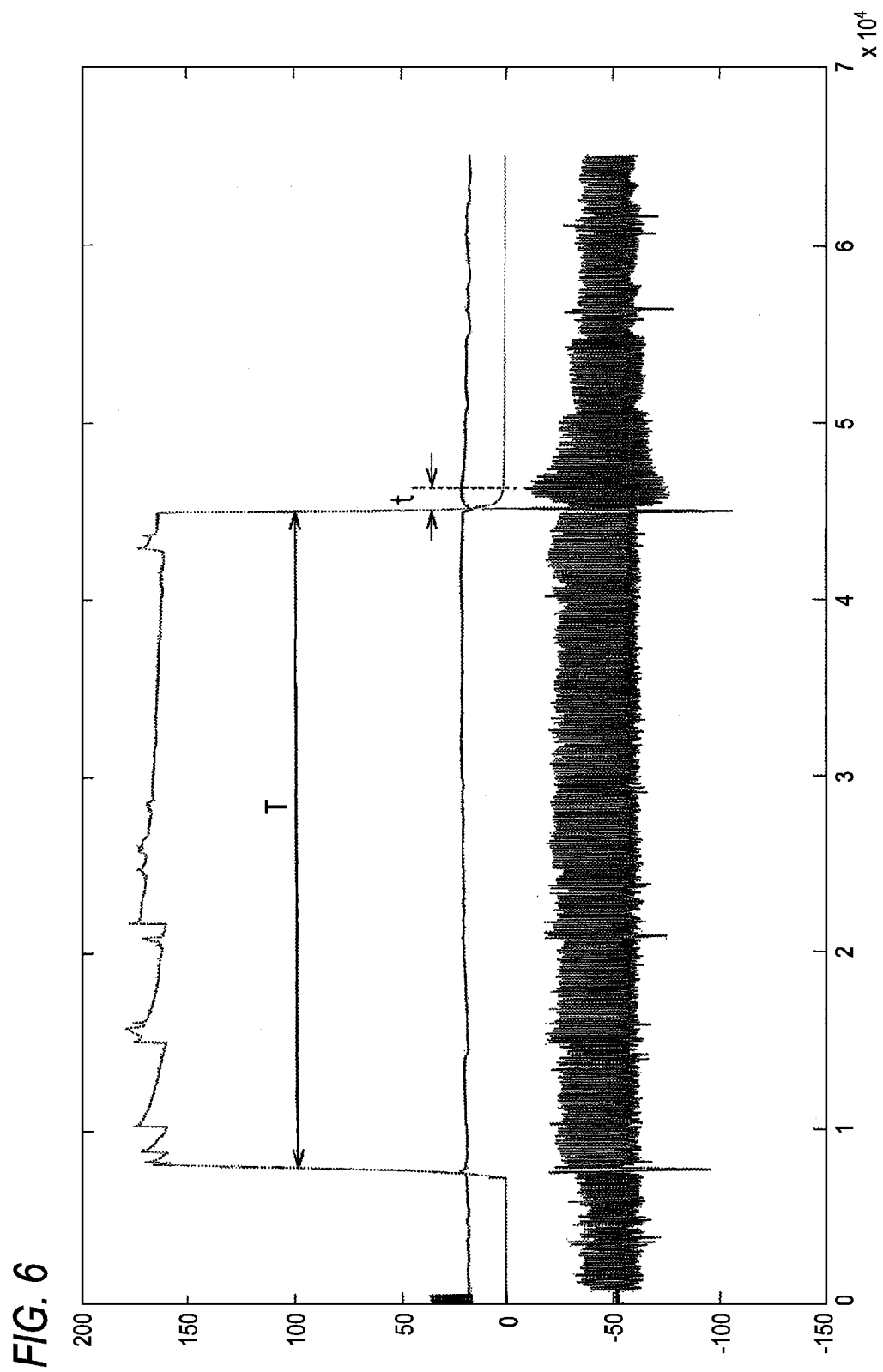
FIG. 6 is a view showing a change of a pulse wave amplitude in the case where the pulse wave measurement is performed after the period of the occlusion of the artery by the embodiment of the apparatus according to the invention.

In the case where, as described above, occlusion of the artery is performed by the first cuff 11, and the pulse wave amplitude is measured in a different portion by the second cuff 51, the amplitude is gradually increased from the end of the pressurization period T, and the pulse wave amplitude reaches the maximum value after the elapse of a certain time period t as shown in FIG. 6. In the Japanese patent application (JP-A-2009-273870), which is the related art, of the inventors of the present patent application, in the case where the pulse wave amplitude is measured in the same portion by the cuff for performing occlusion of the artery, it is measured that the pulse wave amplitude suddenly reaches the maximum value immediately after the end of the pressurization period T as shown in FIG. 5.

Figure 7:
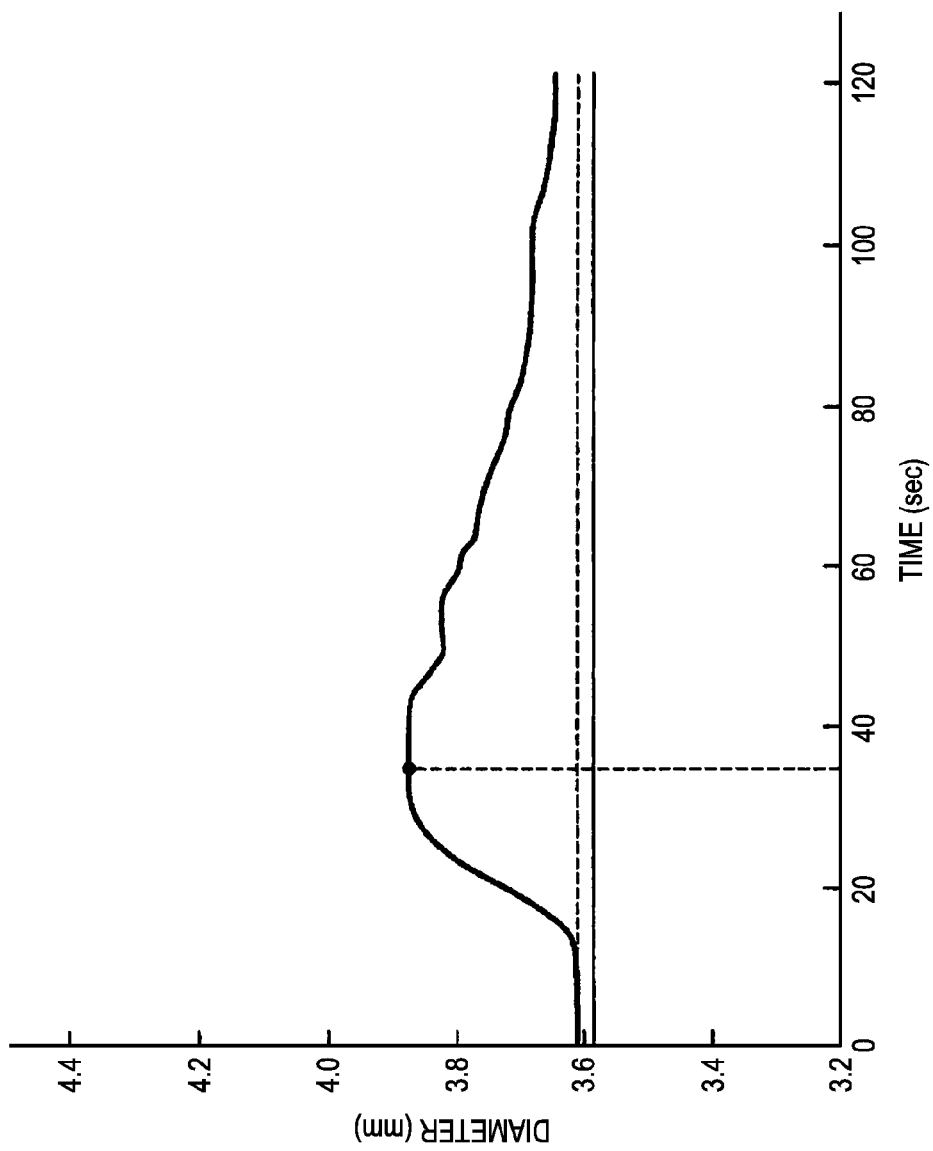
FIG. 7 is a view showing a time-dependent change in the case where a measurement of the vessel diameter is performed after the period of the occlusion of the artery by an FMD measurement system.

In a measurement by the FMD measurement system which is a reliable system for measuring a vascular endothelial function, the vessel diameter reaches the maximum value after the elapse of a slight time period from the end of the occlusion of the artery as shown in FIG. 7. From the above, the timing when the pulse wave amplitude which is obtained by the technique of the invention (the technique in which occlusion of the artery is performed by the first cuff 11, and the pulse wave amplitude is measured in a different portion by the second cuff 51) reaches the maximum value is close to that when the vessel diameter reaches the maximum value in the measurement by the FMD measurement system. This means that the pressure stimulation in a different portion produces a result which is close to the feature of the change of the vessel diameter that is obtained by the FMD measurement using an ultrasonic echo system. Therefore, it is seen that a further accurate measurement is performed.

Figure 8:
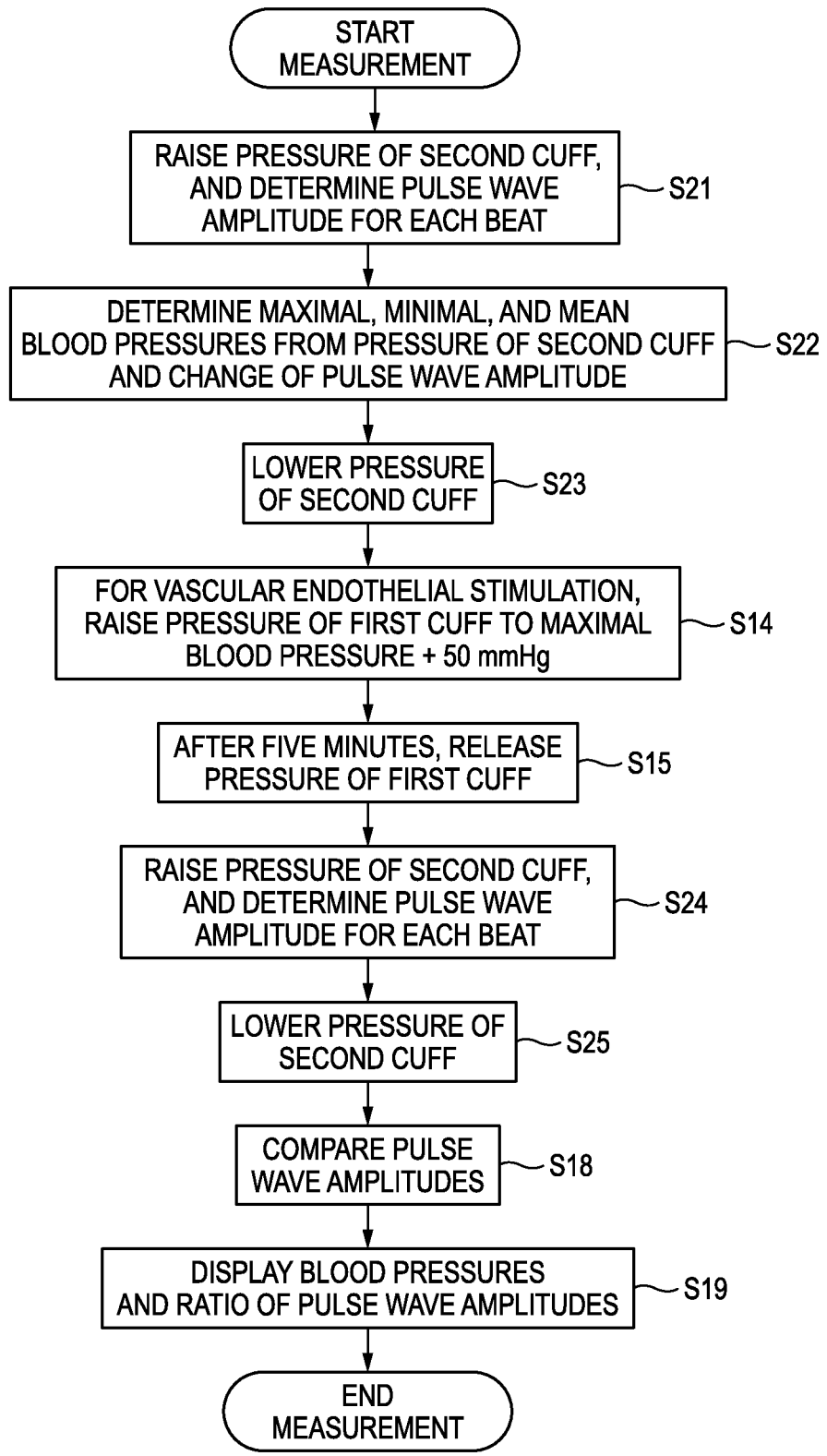
FIG. 8 is a flowchart illustrating a pulse wave measuring operation which is performed in a process of pressurizing the cuff pressure by the embodiment of the apparatus according to the invention.

In the embodiment, the pulse wave amplitude is measured during the process of depressurizing the cuff pressure. Alternatively, as shown in the flowchart of FIG. 8, the measurement may be performed during the process of pressurizing the cuff pressure. Namely, under the control of the controlling unit 20, in the state where the second valve 53 is closed, the air is sent from the second pump 52 to the second cuff 51 to raise the cuff pressure, and, during the process of pressurizing the cuff pressure, the pulse wave amplitude for each beat is detected by the pulse wave detecting unit 32 (S21).

Figure 9:
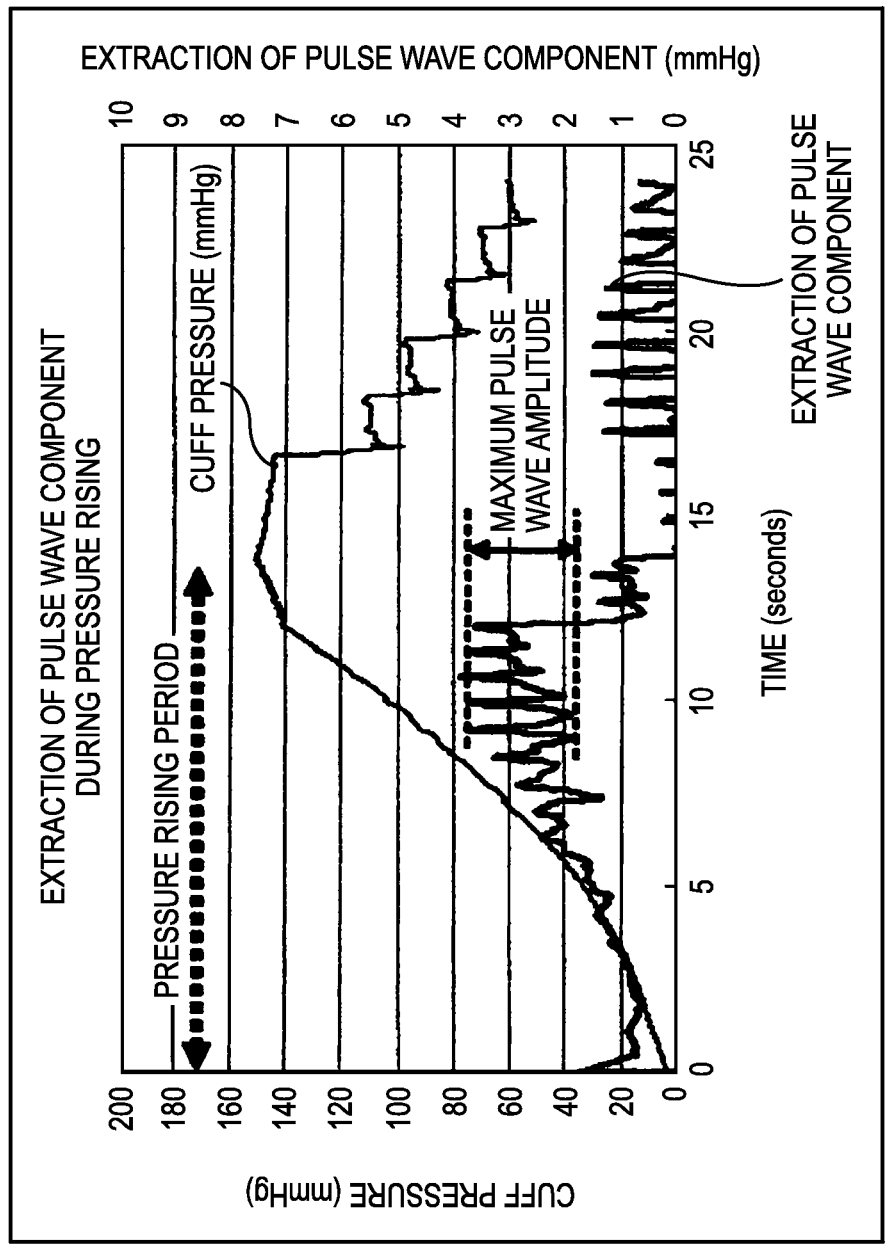
FIG. 9 is a view showing a measurement waveform in the case where the pulse wave measuring operation is performed in the process of pressurizing the cuff pressure by the embodiment of the apparatus according to the invention.

Furthermore, the cuff pressure detecting unit 31 detects the cuff pressure from the output of the second pressure sensor 54, and, on the basis of the cuff pressure and the pulse wave amplitude, the analyzing unit 33 determines the maximal, minimal, and mean blood pressures, and obtains a representative pulse wave amplitude (S22). The representative pulse wave amplitude is obtained by statistically processing the pulse wave amplitude which is obtained in the pressurization period shown in FIG. 9. The pulse wave amplitude in the pressurization period is obtained as shown in FIG. 9, and hence the maximum pulse wave amplitude is obtained. In the pressurization period, when the cuff pressure is equal to the mean blood pressure, the pulse wave amplitude is maximum, and the amplitude is set as the maximum pulse wave amplitude. In the case where the mean blood pressure is previously known, therefore, pressurization to a pressure which is equal to or higher than the mean blood pressure is not necessary in order to obtain the maximum pulse wave, and the burden on the subject is reduced.

After the pressurizing period which is adequately set, the second valve 53 is opened to lower the pressure of the second cuff 51 (S23), processes such as the occlusion of the artery by the first cuff 11 and its cancellation in steps S14 and S15 which are identical with those of the embodiment shown in the flowchart of FIG. 4 are performed, the pressure of the second cuff 51 is then raised, and, during the process of raising the cuff pressure of the second cuff 51, the pulse wave amplitude for each beat is detected by the pulse wave detecting unit 32 (S24). The process in step S24 is identical with steps S21 and S22. After the process, the pressure of the second cuff 51 is lowered (S25), and processes of steps S18 and S19 which are identical with those shown in the flowchart of FIG. 4 are performed.

In FIGS. 4 and 8, as described above, the pulse wave amplitude for each beat is determined during the lowering of the pressure of the second cuff (S12, S17), or the rising of the pressure (S21, S24). Alternatively, in a state where the pressure of the second cuff is kept constant (at a constant pressure), the pulse wave amplitude for each beat may be determined. For example, the constant pressure is about 20 mmHg.

In the case where, in the state where the pressure of the second cuff is kept constant (at a constant pressure), the pulse wave amplitude for each beat is determined, the first cuff and the second cuff may be identical with each other, or a single cuff may be used. In such a case, the configuration of FIG. 1 is modified so that the second cuff 51, the second pump 52, the second valve 53, and the second sensor 54 are removed away, the first cuff 11 is provided with the function of the second cuff 51, the first pump 12 is provided with the function of the second pump 52, the first valve 13 is provided with the function of the second valve 53, and the first sensor 14 is provided with the function of the second sensor 54.

Figure 11:
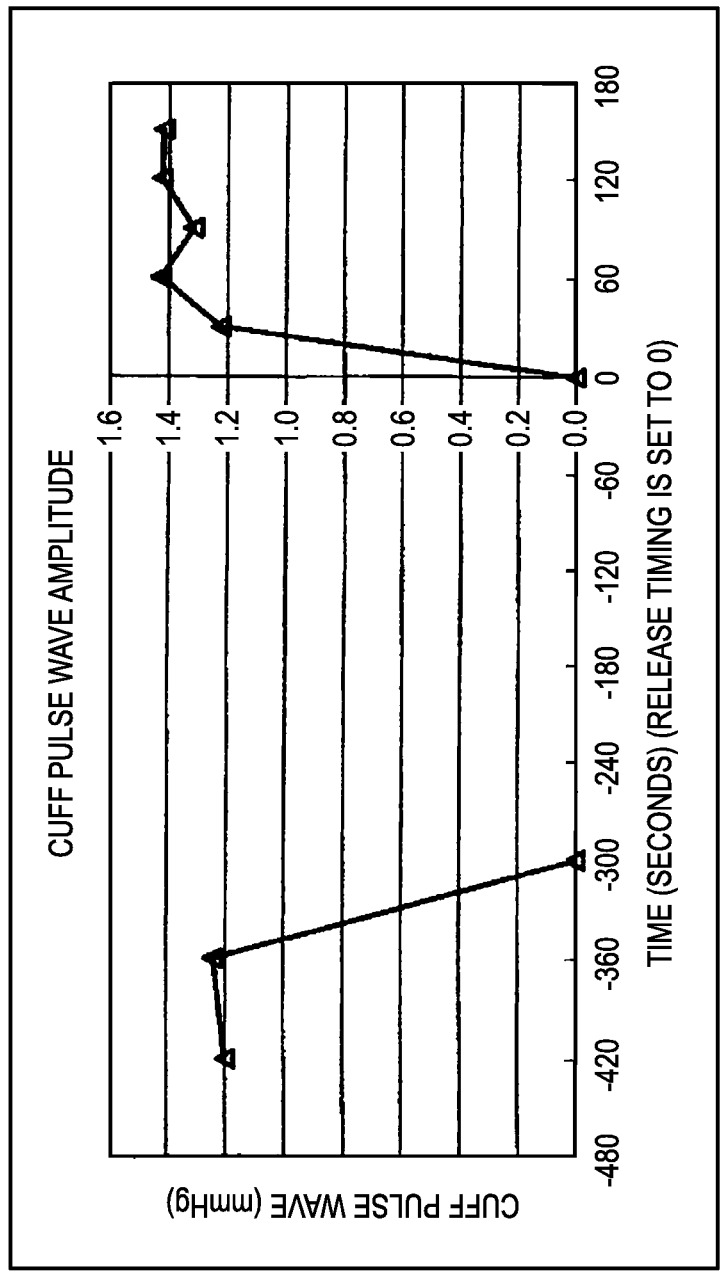
FIG. 11 is a view showing an example of information displayed by the embodiment of the apparatus according to the invention.
Figure 12:
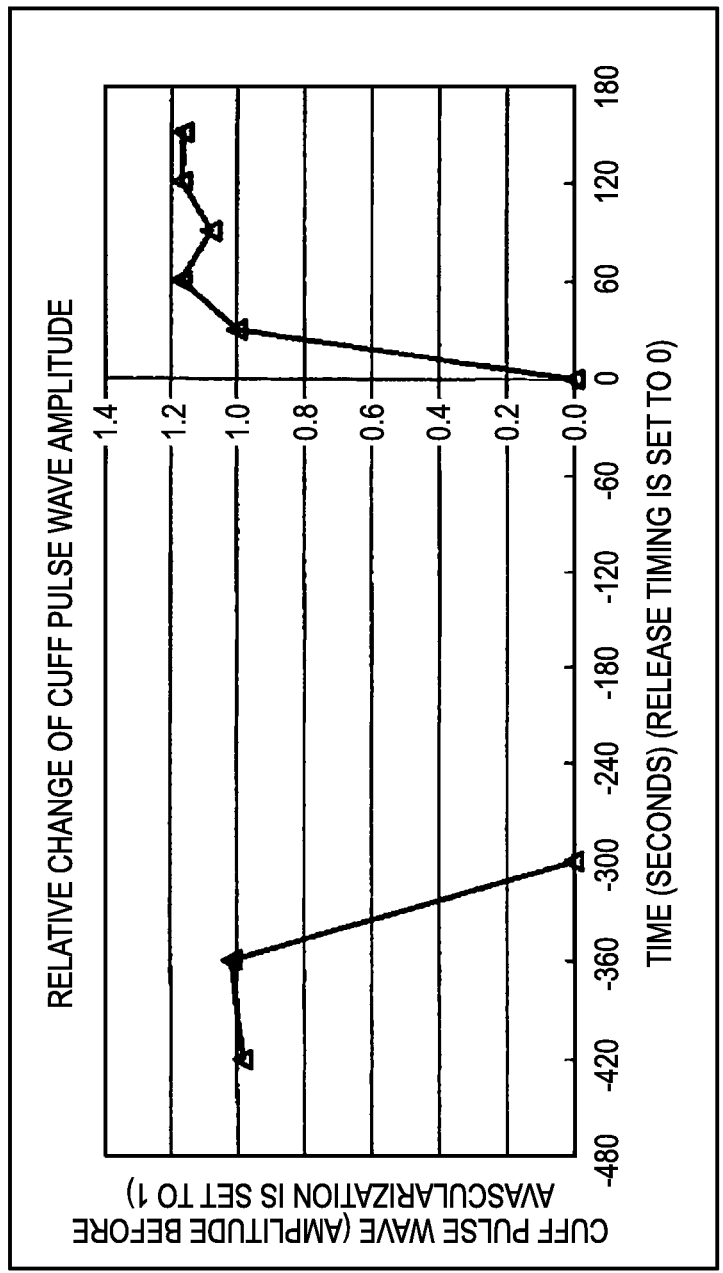
FIG. 12 is a view showing an example of information displayed by the embodiment of the apparatus according to the invention.

The apparatus for evaluating a vascular endothelial function displays the blood pressure values together with a result of a comparison of the pulse wave amplitudes which are obtained as described above, on the displaying unit 40 as shown in FIG. 10. As the blood pressure values, values of a preset one of the pressurization periods Tp and Ta using the second cuff 51 are displayed. The apparatus for evaluating a vascular endothelial function may produce a graph which is shown in FIG. 11, and in which the value of the cuff pulse wave amplitude is plotted in time series, and display the graph on the displaying unit 40. Furthermore, the apparatus may produce a graph which is shown in FIG. 12, and in which a ratio of the representative pulse wave amplitude B to the representative pulse wave amplitude A is plotted in time series, and display the graph on the displaying unit 40.

Figure 14:
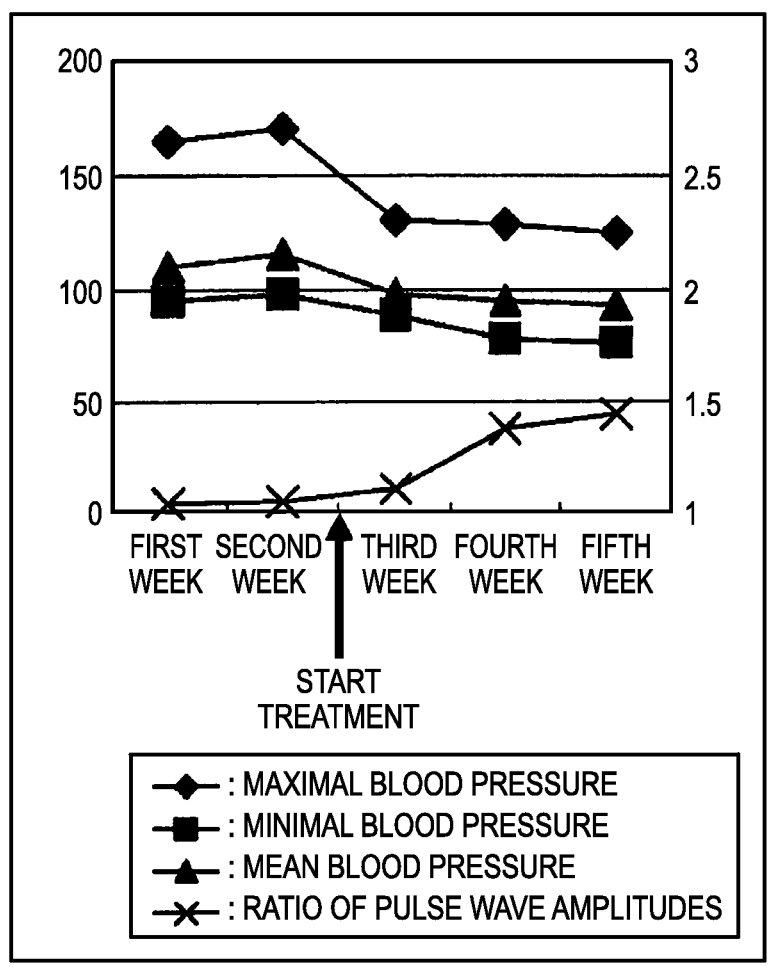
FIG. 14 is a view showing an example of information displayed by the embodiment of the apparatus according to the invention.

Moreover, history information of measured data may be caused to remain, and the trend may be displayed on the displaying unit 40 in the form of a list as shown in FIG. 13. From the data of the table shown in FIG. 13, the graph shown in FIG. 14 may be produced, and the trend may be displayed on the displaying unit 40. The example of FIGS. 13 and 14 shows data in the case where subjects with high blood pressure were treated after the third week. It is very clear that, after the third week, the blood pressure is lowered and the pulse wave amplitude ratio is improved from "1" to a value in the vicinity of "1.5".

The process in which, as described above, continuous pressure stimulation is performed by the cuff pressure on a body part of the subject for a predetermined time means the followings. Normal vascular endothelial cells are caused to produce vasodepressor materials such as nitric monoxide (NO) by stimulation due to a blood flow or medication. When the vascular endothelial function is lowered, the ability of producing vasodepressor materials is lowered. When the degree of vasodilation by stimulation is measured, therefore, it is possible to evaluate the vascular endothelial function.

The relationships among the inner vascular pressure, the cuff pressure, and the pulse wave amplitude contained in the cuff pressure signal can be described as follows. First, it is known that, when the inner vascular pressure and the cuff pressure are equal to each other, the vascular compliance is maximum. The non-invasive blood pressure measurement by the oscillometric method uses the property. When the cuff pressure is equal to the mean blood pressure, the difference between the maximal and minimal blood pressures in a vessel, i.e., the vessel volumetric change due to the pulse pressure is maximum. Therefore, the maximum pulse wave amplitudes A and B are detected in the pressurization periods Ta and Tp using the second cuff 51, and set as representative pulse wave amplitudes.

A representative pulse wave amplitude is a pulse wave amplitude under conditions where the relationships between the cuff pressure and the inner vascular pressure are substantially identical with one another in a series of pulse wave amplitude changes. Therefore, pulse wave amplitudes at application of the same predetermined cuff pressure may be employed in place of the maximum pulse wave amplitudes A and B. In any case, a representative pulse wave amplitude can be obtained by statistically processing the pulse wave amplitude which is obtained in the measurement period using the second cuff 51.

Figure 15A:
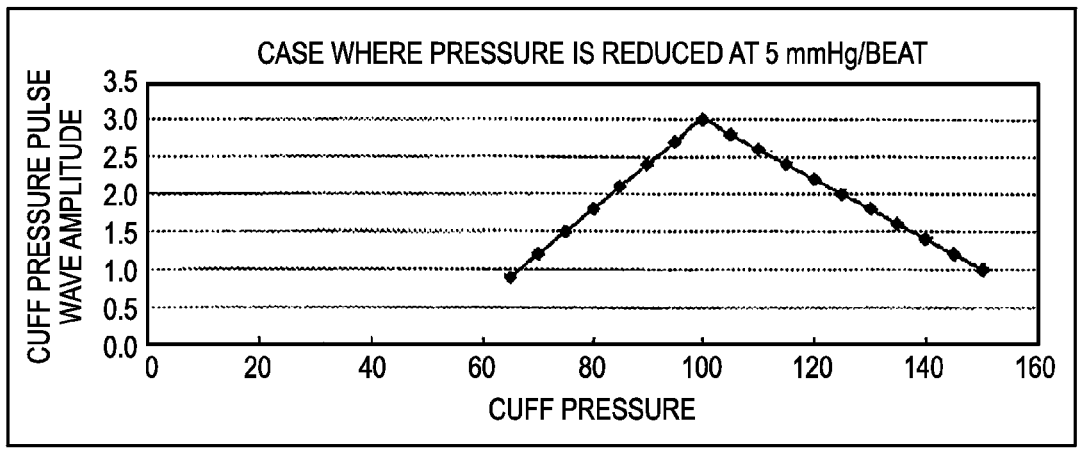
FIGS. 15A to 15C are views illustrating statistical processing which is performed by the embodiment of the apparatus according to the invention.
Figure 15B:
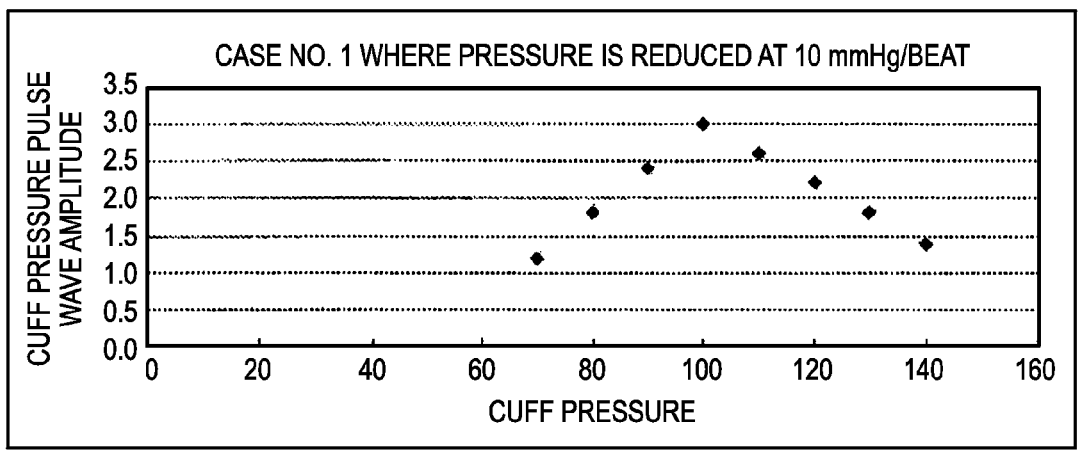
Figure 15C:
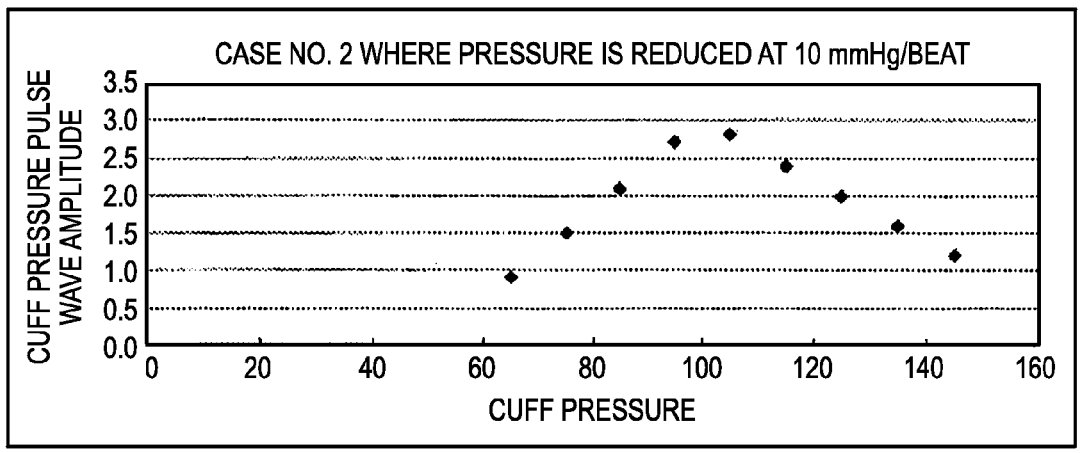

The pulse pressure is repeated due to contraction and expansion of the heart. Therefore, the relationships between the pulse pressure and the change of the cuff pressure are not constant. FIGS. 15A to 15C show relationships between the cuff pressure and the pulse wave amplitude. FIG. 15A shows a pulse wave amplitude in the case where the pressure is reduced at the rate of 5 mmHg per beat, and FIGS. 15B and 15C show a pulse wave amplitude in the case where the reduction rate is increased. In FIGS. 15B and 15C, the relationships between the reduction start timing and the pulse beat are different from each other.

In FIGS. 15B and 15C, the maximum pulse wave amplitudes are 3 mmHg and 2.8 mmHg, respectively, and there is a difference of 0.2 mmHg. The analyzing unit 33 performs statistical processing in which the mean value of pulse wave amplitudes at predetermined number (for example, three) of points in the neighborhood of the maximum pulse wave amplitude is calculated among obtained pulse wave amplitudes. In the example, when the mean value of pulse wave amplitudes at three points is calculated, the obtained mean value in FIG. 15B is 2.67 mmHg, and that in FIG. 15C is 2.64 mmHg. The difference can be reduced. Therefore, it is possible to obtain a value which is preferred as a representative pulse wave amplitude.

In the above description, the pressurization periods Tp and Ta for measuring the pulse wave amplitude by using the second cuff 51 are realized before and after the pressurization period T for vascular endothelial stimulation, and one measurement is performed in each of the pressurization periods Tp and Ta for measuring the pulse wave amplitude. Alternatively, a plurality of measurements may be performed. In the alternative, the numbers of measurements before and after the pressurization period may be different from each other.

Figure 16A:
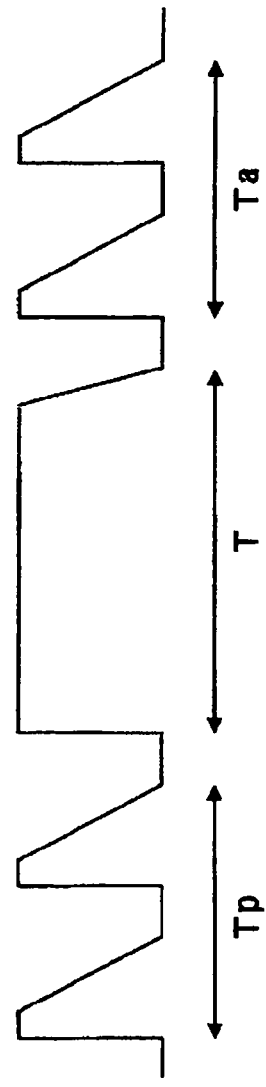
FIGS. 16A and 16B are views showing second examples of the pulse wave measurement which is performed by the embodiment of the apparatus according to the invention, and the period of the occlusion of the artery.
Figure 16B:
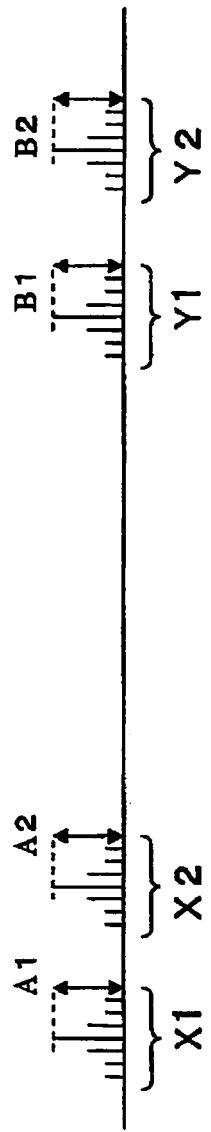

FIGS. 16A and 16B show an example in which two measurements are performed in each of the measurement periods Tp and Ta for a pulse wave amplitude. In this example, during the pressurization period Tp, the analyzing unit 33 obtains measured-value groups X1 and X2 as a result of the two measurements. Each of the measured-value groups X1 and X2 is statistically processed to obtain representative pulse wave amplitudes A1 and A2. In this example, maximum pulse wave amplitudes A1 and A2 are obtained as shown in FIG. 16B.

Also during the pressurization period Ta shown in FIG. 16A, measured-value groups Y1 and Y2 are obtained as a result of the two measurements. The analyzing unit 33 performs statistical processing on the measured-value groups Y1 and Y2, and obtains maximum pulse wave amplitudes B1 and B2 which are representative pulse wave amplitudes as shown FIG. 16B.

Furthermore, the analyzing unit 33 performs statistical processing for obtaining the respective mean values on the maximum pulse wave amplitudes A1 and A2 and maximum pulse wave amplitudes B1 and B2 which are obtained in the above-described processes, to obtain final representative pulse wave amplitudes. Namely, (A1+A2)/2 and (B1+B2)/2 are obtained as representative pulse wave amplitudes. As a result of the above-described measurements and processing, errors can be leveled, and highly accurate evaluation is enabled.

The mean values of (A1+A2)/2 and (B1+B2)/2 which are obtained as described above are compared with each other by the analyzing unit 33, {(B1+B2)/2}/{(A1+A2)/2} is calculated by means of division, and the calculation result is displayed together with the blood pressure value on the displaying unit 40.

Other measurement technique and statistical processing will be described. The vasodilation due to vascular endothelial stimulation derived from occlusion of the artery by the first cuff 11 and its release is gradually increased after the release of the occlusion of the artery to reach the peak after several tens of seconds, and thereafter is reduced for several minutes. Based on the peak, it is possible to evaluate the degree of vasodilation. After the vascular endothelial stimulation using the first cuff 11, the maximum value of the pulse wave amplitude is measured several times by using the second cuff 51, and a maximum one of the maximum values is set as the pulse wave amplitude in the vasodilation, thereby obtaining the peak of the vasodilation.

Figure 17A:
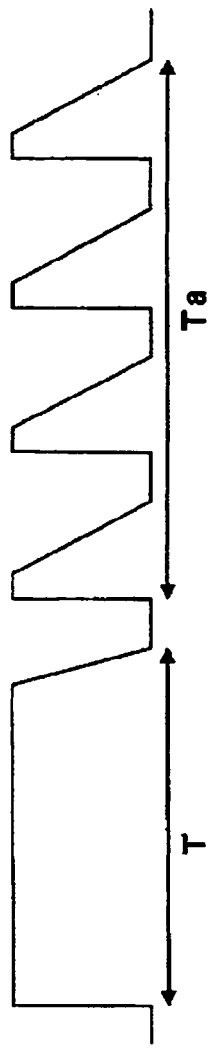
FIGS. 17A to 17C are views showing third examples of the pulse wave measurement which is performed by the embodiment of the apparatus according to the invention, and the period of the occlusion of the artery.
Figure 17B:
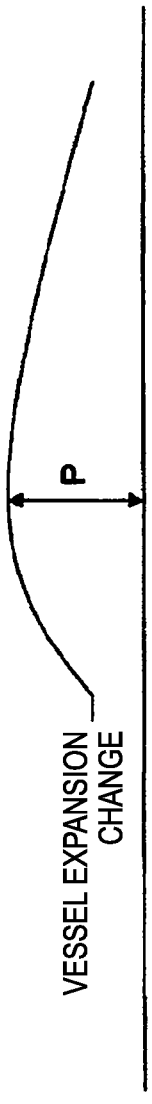
Figure 17C:
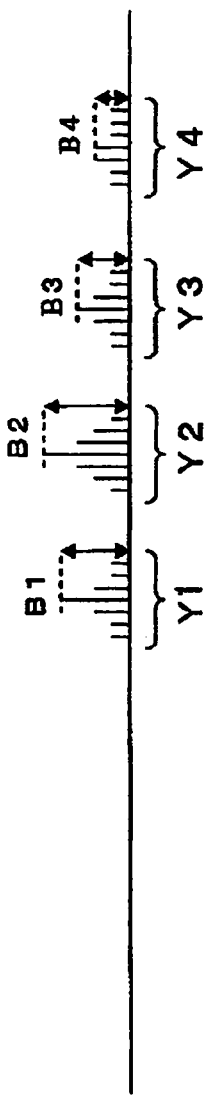

As shown in FIG. 17A, specifically, the pressurization period Ta for measuring the pulse wave amplitude by using the second cuff 51 is realized after the pressurization period T using the first cuff 11. In the example, four measurements are performed. As a result of the four measurements, measured-value groups Y1, Y2, Y3, and Y4 are obtained. In this case, the vasodilation changes as shown FIG. 17B, and it is estimated that a peak P exists in the vicinity of the measured-value group Y2. The analyzing unit 33 performs statistical processing on the measured-value groups Y1, Y2, Y3, and Y4, and, as shown in FIG. 17C, obtains maximum pulse wave amplitudes B1, B2, B3, and B4 which are representative pulse wave amplitudes.

The analyzing unit 33 compares the levels of the maximum pulse wave amplitudes B1, B2, B3, and B4 with one another, and selects the maximum maximum pulse wave amplitude B2 as a representative pulse wave amplitude. The maximum maximum pulse wave amplitude B2 is handled in the same manner as the above-described maximum pulse wave amplitude B. Namely, the amplitude is compared in the analyzing unit 33, and a ratio with respect to the maximum pulse wave amplitude which is obtained by the measurement before the pressurization period T is calculated, and displayed together with obtained blood pressure value on the displaying unit 40.

Finally, the vascular compliance will be described. When V indicates the cuff interior volume, P indicates the cuff internal pressure, and the temperature is assumed to be constant, the following expression holds from the gas state equation.

$$P \times V = \text{constant} = k$$

Here, transition advances in the sequence of the vascular volume change $\Delta V \to \to$ the cuff volume change of $-\Delta V \to \to$ the pressure change $\Delta P$. Therefore, $$(P+\Delta P) \times (V-\Delta V) = k.$$

When $\Delta P \times \Delta V$ is deemed to be small as compared with the other terms and ignored, $$P \times V + V \times \Delta P - P \times \Delta V = k.$$

Substituting P×V=k, $$V \times \Delta P - P \times \Delta V = 0.$$

$$\Delta V = \Delta P \times V/P \quad \text{(Exp. 1)}$$

Therefore, the cuff pressure change $\Delta P$ is proportional to the vascular volume change $\Delta V$ (in the case where V and P are constant).

It is known that P at which the volume change $\Delta V$ is maximum is the mean blood pressure (because the state where the pressures internal and external of the vessel are balanced with each other is attained). The vascular volume change $\Delta V$ is determined by the pulse pressure $\Delta BP$ (maximal blood pressure − minimal blood pressure) and the vascular compliance C. Namely, following Exp. 2 holds.

$$\Delta V = C \times \Delta BP \quad \text{(Exp. 2)}$$

Here, $\Delta V$ before the pressure stimulation is indicated by $\Delta V1$, $\Delta V$ after the pressure stimulation is indicated by $\Delta V2$, C before the pressure stimulation is indicated by C1, C after the pressure stimulation is indicated by C2, $\Delta P$ before the pressure stimulation is indicated by $\Delta P1$, and $\Delta P$ after the pressure stimulation is indicated by $\Delta P2$. In this case, it is found that the evaluation of the vascular endothelial function can be performed on the basis of the vascular compliance in accordance with following conditions 1 and 2.

Condition 1: the Case where the Maximal, Minimal, and Mean Blood Pressures are not Changed Before and after the Pressure Stimulation In the case where, before and after the pressure stimulation, the mean blood pressure is not changed and the cuff attachment state is not changed, P and V of Exp. 1 are constant. Therefore, a change of $\Delta P$ indicates that of $\Delta V$. In the case where, before and after the pressure stimulation, the maximal and minimal blood pressures are not changed, $\Delta BP$ is constant, and hence the following is attained from Exp. 2.

$$\Delta P2/\Delta P1 = \Delta V2/\Delta V1 = C2/C1$$

When cuff pressure pulse waves are compared with each other, it is possible to compare the vascular compliances (softnesses) with each other.

Condition 2: the Case where the Blood Pressure is Changed Before and after the Pressure Stimulation It remains unchanged that, when the cuff internal pressure is equal to the mean blood pressure, $\Delta V$ indicates the maximum value. From Exp. 2, $\Delta V$ is proportional to $\Delta BP$. When $\Delta V/\Delta BP$ is obtained, therefore, it is possible to obtain a more correct vascular compliance C.

The analyzing unit 33 performs processing in which the vascular compliance is obtained, in addition to the processings in which a result of comparison of pulse waves, and blood pressures are obtained. The analyzing unit 33 divides the detected pulse wave amplitude by the difference between the maximal and minimal blood pressures, to obtain the vascular compliance C. As described above, when the inner vascular pressure and the cuff pressure are equal to each other, the vascular compliance is maximum. The compliance which is to be obtained in this case is not restricted to a value when the inner vascular pressure and the cuff pressure are equal to each other. During the pressurization periods Tp and Ta for measuring the pulse wave amplitude which are set before and after the pressurization period T, compliances for representative pulse wave amplitudes which are respectively obtained in the periods may be obtained. The obtained compliances are displayed on the displaying unit 40, independently or together with the ratio of the pulse wave amplitudes which have been described, and obtained blood pressure values. In this case, data of the measured compliances may be caused to remain as history information, the information may be formed as a table or a graph, and the trend may be displayed on the displaying unit 40.

According to an aspect of the invention, a change in vascular volume before and after the pressure stimulation is measured, so that information which is equivalent to that obtained in the FMD method that is a reliable technique can be easily obtained, and the measurement can be performed by a technique and configuration which are similar to those of the blood pressure measurement that is currently widely performed, so that skills are not required.

The vessel volumetric change obtained in the present invention is a change of the vascular volume in an area where a cuff is attached. The cuff-attached area is constant in a series of measurements, and hence the vessel volumetric change can be deemed as a change in vessel sectional area. While a change in vessel diameter is obtained in the FMD method, the square of the vessel diameter can be deemed as the sectional area, and hence a vasodilation phenomenon which is to be obtained can be detected highly sensitively.

According to an aspect of the invention, an idle period when the cuff pressurization is stopped exists between the pressure stimulation and the pulse wave measurement. Therefore, a continuous vessel blocking period is kept to the minimum, so that the burden on the subject can be reduced.

According to an aspect of the invention, a sensor other than the cuff is not necessary. Consequently, the present invention is advantageous in operation.

According to an aspect of the invention, it is requested only to measure the amplitude of the pulse wave, and hence an analyzing unit is not required to have a high processing capacity.

It is known that the cuff pressure indicating the maximum pulse wave amplitude is the mean blood pressure. Irrespective of the level of the blood pressure, when a vessel is compressed by a cuff at a pressure which is equal to the mean blood pressure, the pressures internal and external of the vessel counteract each other, and the force acting in the circumferential direction of the vessel wall is minimized. The maximum pulse wave amplitude is always measured in a state where the force acting in the circumferential direction of the vessel wall is minimum, and therefore the influence of the level of the blood pressure on the measurement result is reduced. According to an aspect of the invention, the maximum pulse wave amplitude in the case where the cuff pressure is changed is measured, whereby the influence of the blood pressure can be reduced.

According to an aspect of the invention, continuous pressure stimulation is performed on a body part of the subject for a predetermined time, and the analyzing unit evaluates the vascular endothelial function by comparing pulse waves before and after the pressure stimulation with each other. Therefore, the configuration and the measurement technique are simplified, and, since the pulse waves before and after the pressure stimulation are proportional to the vessel volumetric change, the comparison of the pulse waves enables the evaluation of the vascular endothelial function to be performed highly accurately. Furthermore, the cuff pressure is detected from the output of the pressure sensor connected to the second cuff which is wound around the second portion of the body of the subject. Therefore, an influence of ischemia due to vascular blockage is not exerted in the portion where the pulse wave is measured, and the vascular endothelial function can be evaluated highly accurately in a similar manner as a measurement using an ultrasonic echo system.

Usual blood pressure measurement involves compression which is performed on the subject by a cuff for several tens of seconds. According to an aspect of the invention, the blood pressure measurement is performed during the process of pressurizing the cuff pressure, and hence the measurement is completed during the process in which the subject is compressed. Therefore, the measurement time can be shortened, and the burden on the subject can be reduced.

According to an aspect of the invention, during the process of pressurizing or depressurizing the cuff pressure, the blood pressure measurement is performed in the second portion such as an arm of the body by using the second cuff. Unlike the case of a peripheral artery, therefore, a highly accurate measurement is enabled without being affected by the sympathetic control.

According to an aspect of the invention, the two cuffs, i.e., the measurement cuff and the pressure stimulation cuff are separately used. Therefore, a further accurate measurement which is hardly influenced by ischemia due to vascular blockage that is caused by pressure stimulation is enabled.

According to an aspect of the invention, the measurement cuff and the pressure stimulation cuff are configured by two cuffs or one cuff, processing in which the cuff pressure is raised from an atmosphere pressure to a pressure that is equal to or higher than the mean blood pressure of the subject, and then lowered to a pressure that is equal to or lower than the minimal blood pressure is performed at least one time, and the analyzing unit statistically processes and compares changes of the pulse wave during the change of the cuff pressure. Therefore, the pulse wave measurement is enabled by the raising of the mean blood pressure, and can be adequately performed without imposing a physical burden on the subject, and while shortening the pressurization time.

What is claimed is:

1. An apparatus for evaluating a vascular endothelial function, the apparatus comprising:
a first cuff, to be wound around a first portion of a body part of a subject;
a second cuff, to be wound around a second portion of the body part of the subject, which is on an upstream side, closer to a heart of the subject, of the first cuff;
a cuff pressure controller, configured to control a cuff pressure of each of the first and second cuffs, configured to perform first cuff pressure processing using the second cuff that includes a first process and a second process subsequent to the first process, the first process in which the cuff pressure of the second cuff is raised from an atmosphere pressure to a pressure that is equal to or higher than a mean blood pressure of the subject, and the second process in which the cuff pressure of the second cuff is lowered to a pressure that is equal to or lower than a minimal blood pressure, configured to perform continuous pressure stimulation on the first body part of the subject for a time period by using the first cuff in response to performing the first cuff pressure processing, and configured to perform second cuff pressure processing using the second cuff that includes the first process and the second process subsequent to the first process in response to performing the continuous pressure stimulation;

a cuff pressure detector, configured to detect the cuff pressure of the second cuff from an output of a pressure sensor connected to the second cuff;

a pulse wave detector, configured to detect, from the output of the pressure sensor, first pulse waves during the first cuff pressure processing and second pulse waves during the second cuff pressure processing; and an analyzer, configured to evaluate the vascular endothelial function by applying statistical processing on changes of the first pulse waves while the cuff pressure controller performs the first cuff pressure processing to obtain a first average value of amplitudes of the first pulse waves comprising at least one pulse wave occurring prior to a pulse wave having a maximum amplitude while the cuff pressure controller performs the first cuff pressure processing, the pulse wave having the maximum amplitude while the cuff pressure controller performs the first cuff pressure processing, and at least n pulse wave occurring after the pulse wave having the maximum amplitude while the cuff pressure controller performs the first cuff pressure processing, and the statistical processing on changes of the second pulse waves while the cuff pressure controller performs the second cuff pressure processing to obtain a second average value of amplitudes of the second pulse waves comprising at least one pulse wave occurring prior to a pulse wave having a maximum amplitude while the cuff pressure controller performs the second cuff pressure processing, the pulse wave having the maximum amplitude while the cuff pressure controller performs the second cuff pressure processing, and at least one pulse wave occurring after the pulse wave having the maximum amplitude while the cuff pressure controller performs the second cuff pressure processing, and comparing the first average value to the second average value.

2. The apparatus according to claim 1, wherein the comparing comprises calculating an amplitude ratio of the first pulse waves and the second pulse waves.

3. The apparatus according to claim 1, wherein the continuous pressure stimulation performed by the cuff pressure controller is a constant pressure.

4. The apparatus according to claim 1, wherein the statistical processing comprises obtaining a maximum value in amplitudes of pulse waves detected in the first process or the second process.

5. The apparatus according claim 1, wherein the analyzer performs processing in which an amplitude of each of the pulse waves is divided by a difference between a maximal blood pressure of the subject and a minimal blood pressure of the subject, to obtain vascular compliance.

6. The apparatus according to claim 1, further comprising a display, wherein the analyzer calculates a blood pressure value from each pulse wave, and the display displays the blood pressure value together with a result of the comparing.

7. The apparatus according to claim 1, wherein the first portion of the body part around which the first cuff is adapted to be wound and the second portion of the body part around which the second cuff adapted to be wound are parts of one of four limbs of a body of the subject.

8. The apparatus according to claim 1, wherein the first portion of the body part around which the first cuff is adapted to be wound is placed on a peripheral side of a body of the subject with respect to the second portion of the body part around which the second cuff is adapted to be wound.

* * * * *